United States Patent [19]
Kross

[11] Patent Number: 5,628,959
[45] Date of Patent: May 13, 1997

[54] COMPOSITION AND METHODS FOR STERILIZING DIALYZERS

[75] Inventor: Robert D. Kross, Bellmore, N.Y.

[73] Assignee: Alcide Corporation, Redmond, Wash.

[21] Appl. No.: 417,061

[22] Filed: Apr. 3, 1995

[51] Int. Cl.$^6$ .......................... A01N 25/02; A01N 59/08; A61L 2/18; B08B 3/08
[52] U.S. Cl. .................. 422/37; 134/27; 422/44; 424/665
[58] Field of Search .................... 422/28, 37, 44; 134/22.13, 22.14, 22.16, 22.17, 27, 28; 424/661, 665

[56] References Cited

U.S. PATENT DOCUMENTS

| | | | |
|---|---|---|---|
| 4,104,190 | 8/1978 | Hartshorn | 424/149 X |
| 4,673,506 | 6/1987 | Henne et al. | 422/34 X |
| 4,690,772 | 9/1987 | Tell et al. | 252/106 |
| 5,078,967 | 1/1992 | Aixala | 422/37 |
| 5,178,830 | 1/1993 | Aixala | 422/37 |
| 5,185,161 | 2/1993 | Davidson et al. | 424/665 |
| 5,192,459 | 3/1993 | Tell et al. | 424/665 X |

*Primary Examiner*—Robert J. Warden
*Assistant Examiner*—E. Leigh Dawson
*Attorney, Agent, or Firm*—Seed and Berry LLP

[57] ABSTRACT

Compositions and methods are provided for sterilizing hemodialysis apparatus, particularly for reprocessing dialyzers in a manner that minimizes membrane perforations. The compositions contain a protic acid and a metal chlorite, and have a pH of at least about 2.3 and no greater than 4.2. Methods of this invention include contacting both the blood side and the dialysate side of a dialysis membrane with the composition, followed by first displacing the composition on the dialysate side with water or an aqueous alkali buffer having a pH in excess of about 6.0, such that the pH of the composition on the blood side of the dialysis membrane increases to at least about 5.0. The composition on the blood side is then displaced with saline. In a further embodiment, the composition has a pH ranging from 3.3 to 4.2, and the amount of chlorite ion in the form of chlorous acid ranges from 0.5% to 5.0% by weight of the total amount of chlorite ion in the composition. In this embodiment, the composition may be employed without associated membrane degradation by using existing hemodialysis set-up techniques, except that dialysate displacement on the dialysate side precedes saline displacement of blood side.

26 Claims, 1 Drawing Sheet

COMPOSITION AND METHODS FOR STERILIZING DIALYZERS

TECHNICAL FIELD

This invention relates generally to compositions and methods for sterilizing dialysis apparatuses and, more specifically, to the use of chlorous acid-containing compositions for reprocessing dialyzers.

BACKGROUND OF THE INVENTION

There are over 100,000 individuals in the United States whose kidney functions do not provide adequate urinary clearance of accumulated blood waste products. Approximately 90% of this population relies on hemodialysis (i.e., the so-called "artificial kidney") to remove impurities and fluids from their blood. Hemodialysis is also used in other instances, such as a direct or supportive measure during the treatment of certain heart conditions and scleroderma, and in the removal of metabolites from methyl alcohol poisoning.

The artificial kidney is a mechanical-chemical approach which utilizes both diffusion and ultrafiltration to remove impurities and fluids from blood. In dialysis, the blood of a patient is circulated from the patient's body into a dialyzer, where it flows over a semi-permeable membrane bathed in a cleansing or "dialysate" solution. Impurities in the blood pass through the membrane into the dialysate solution by diffusion. In addition, due to a difference in pressure between the blood and dialysate solution, excess fluid in the blood is removed by ultrafiltration. This process is known as "hemodialysis", and dialysis patients must generally undergo hemodialysis 2 to 3 times per week for 4–6 hours per treatment.

The first extracorporeal dialyzer was reported in 1960 and used a flat plate device containing blood with a dialysate solution flowing on the other side of a membrane. This was followed in the late 1960s by a twin-coil dialyzer and, soon thereafter, by the current hollow-fiber dialyzer. Hollow-fiber dialyzers are roughly shaped like a flashlight, and consist of 100 micron diameter membrane tubes (typically cellulosic or cellulosic ester based) through which the blood flows, and which are bundled together and immersed in a counter-current flow of dialysate solution. The dialyzer is, in turn, connected to a dialysis machine which contains a number of sensors (e.g., blood flow, blood leaks, blood pressure, etc.), as well as pumps, valves, flow pistons and flow diverters.

The portion of a representative dialysis machine which contains the dialyzer is represented in FIG. 1. More specifically, FIG. 1 illustrates the location of hollow-fiber dialyzer 1, blood flow from the patient 2, blood flow to the patient 3, dialysate solution flow into the dialyzer 4, dialysate solution flow out of the dialyzer 5 and pump 6 which controls blood flow through the dialyzer. Dialysate solution (about 500 ml/minute) is moved into and out of the dialyzer by a series of pumps, one of which extracts a specified amount of spent dialysis fluid from the circuit and replaces it with fresh dialysate. Impurities pass from the blood and into the dialysate by diffusion. In addition, because there is a difference in pressure between the blood and dialysate, excess fluid in the blood is removed by ultrafiltration. Within established safe limits, the trans-membrane pressure is allowed to change freely to any value that results from the dialyzer ultrafiltration rate chosen.

While the price of dialyzers has been significantly reduced since their initial introduction, the annual cost for patients who undergo hemodialysis 2 to 3 times per week with a so-called "single-use dialyzer" is quite high. Accordingly, much attention has been given to cleaning and sterilizing a dialyzer for repeated use by a given patient. In addition to the obvious amortization of equipment cost over the use-life of the dialyzer (i.e., typically greater than 10 reuses), patients experience fewer symptoms of "first-use-syndrome," which occurs when the patient's blood encounters the membrane and plastic components of a new dialyzer. With use, dialyzers become internally coated with the patient's own proteins (e.g., albumen, fibrinogen, globulin and immunological proteins) which minimizes the severity of such first-use reactions in subsequent dialysis sessions. Since reuse of dialyzers was first introduced in the mid-1960's, evidence has been accumulating that this practice is quite effective and, provided the dialyzer is adequately sterilized between uses, reuse has not been associated with any increase in the rate of infection resulting from dialysis.

To date, the most prevalent and least expensive hemodialyzer reprocessing sterilant has been formaldehyde, which is generally used in the form of a 4% aqueous solution. Formaldehyde is now used in 43% of the hemodialysis centers that reprocess dialyzers. However, those operating in the industry are becoming increasingly reluctant to use formaldehyde because of (a) the antibody formation which formaldehyde provokes, (b) the status of formaldehyde as a co-carcinogen and (c) formaldehyde's overall noxiousness in handling. Similar problems are associated with the related sterilant glutaraldehyde, used in 8% of reprocessing. A more recent sterilant is based on a peracetic acid/hydrogen peroxide combination, and accounts for 49% of reuse sterilant. This system, however, has been associated with an increased level of morbidity in patients exposed to dialyzers reprocessed using this sterilant.

A more effective and more compatible sterilant has been identified, and is based on the cidal species associated with chlorous acid. Such a sterilant was introduced into the hemodialyzer processing market by Alcide Corporation in 1985 under the trade name RenNew-D. The technology of this sterilant involved the combination of lactic acid with a metal chlorite to yield chlorous acid-containing disinfecting compositions. One such chlorous acid system was found to be more effective against bacteria (and bacterial spores) compared to a 4% aqueous formaldehyde solution, and was also able to destroy certain water-borne microorganisms (such as *Mycobacteria chelonei*) which had caused septic outbreaks and deaths in a number of clinics using formaldehyde for hemodialyzer reprocessing. Dialyzer reuse lifetimes were also significantly greater with the chlorous acid system, and the solutions were more "user friendly" than the formaldehyde-based and peracetic/peroxide-based sterilant systems. In addition, and in contrast to other dialyzer sterilants, the chlorous acid system did not denature the inner-protein coatings of dialyzer surfaces.

Practitioners did, however, experience certain problems with the chlorous acid sterilant RenNew-D. Specifically, random perforations appeared in several of the many blood-bearing cellulosic microtubules in dialyzers which had been treated with this product. These "holes" apparently resulted in several cases of septicemia in patients who had been reconnected to the disinfected dialyzers, where bacteria and/or bacterial fragments in the non-sterile dialysate solution passed through the membrane perforations into the patient's blood stream. This problem resulted in the product's subsequent removal from the market.

While significant advances have been made in the field of hemodialysis, particularly with regard to reprocessing dialyzers for multiple reuse by a single patient, significant disadvantages are encountered with existing sterilant solutions used for reprocessing. Accordingly, there is a need in the art for improved sterilant compositions suitable for use as reprocessing sterilants, as well as methods relating to their use. The present invention fulfills these needs, arid provides further related advantages.

SUMMARY OF THE INVENTION

In brief, this invention is directed to compositions and methods for sterilizing dialyzers for multiple reuse by a single patient.

In one embodiment, the composition is an aqueous sterilant containing a protic acid and a metal chlorite, and having a pH no greater than 4.2. The blood side and the dialysate side of a dialyzer are contacted with the sterilant for a sufficient time to sterilize the same. The sterilant on the dialysate side of the dialyzer is then replaced with an aqueous solution having a pH of at least about 6.0, which is maintained within the dialysate side of the dialyzer for a period of time sufficient to cause the pH of the sterilant on the blood side of the dialyzer to increase to at least about 5.0. This pH-adjusted sterilant on the blood side of the dialyzer is then displaced with an isotonic saline solution.

In a preferred embodiment of this invention, the sterilant on the dialysate side of the dialyzer is displaced with an aqueous solution having a pH of at least about 6.0 and containing an alkali ion. The pH-adjusted sterilant on the blood side of the dialyzer is then displaced with an isotonic saline solution.

In another preferred embodiment, the pH of the sterilant containing the protic acid and the metal chlorite has a pH ranging from 3.3 to 4.2. In this embodiment, the sterilant on the dialysate side of the dialyzer may be replaced with a dialysate solution, followed by displacement of the sterilant on the blood side of the dialyzer with isotonic saline.

Other objects and advantages of the present invention will become apparent from the following detailed description and representative examples.

DETAILED DESCRIPTION OF THE INVENTION

Figure 1:
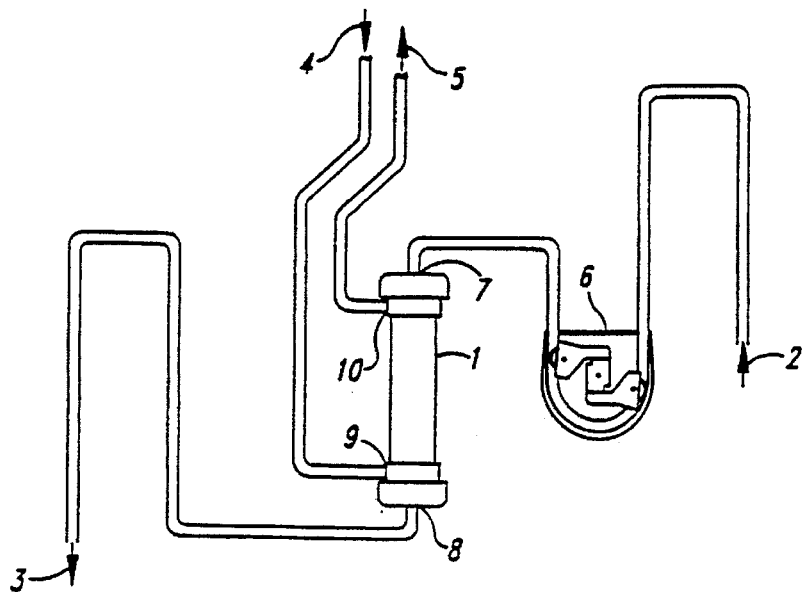
FIG. 1 is a representation of a hemodialysis apparatus illustrating the flow of a patient's blood and a cleansing dialysate solution through a dialyzer.

In general, the present invention is directed to compositions and methods for sterilizing dialyzers for reuse by a dialysis patient. The compositions of this invention are referred to as "sterilants" and are aqueous solutions containing a protic acid and chlorite which, when combined, form chlorous acid. Thus, the sterilants of this invention may also be referred to as "chlorous acid generating" compositions. Such sterilants may be formed by combining a protic acid and chlorite ion (typically in the form of a metal chlorite) in an aqueous solution. The aqueous sterilant may then be used to sterilize a dialyzer by contacting the same with the sterilant as disclosed in greater detail below.

In the practice of this invention, any protic acid (or combination of protic acids) may be used in the generation of the sterilant, including both organic and inorganic acids. Representative organic acids include, but are not limited to, citric, lactic, malic, tartaric, glycolic and mandelic acids. Typically, organic acids having a pK ranging from 2.8 to 4.2 are suitable, and malic acid is preferred. Inorganic acids include, but are not limited to, sulfuric, hydrochloric, nitric and phosphoric acids. The chlorite ion of the sterilant is preferably produced by the aqueous disassociation of a water-soluble chlorite such as a metal chlorite, including both alkali metal chlorites and alkaline earth metal chlorites. To this end, sodium chlorite and potassium chlorite are preferred, with sodium chlorite being particularly preferred.

It has been found that control of the pH of the sterilant, as well as the amount of chloride ion ($Cl^-$) present in the sterilant, is critical to preserve the integrity of the dialysis membrane of the dialyzer over repeated sterilizations. A sterilant having a low pH in the presence of chloride ion will result in increased formation of chlorous acid and its degradation products. At low levels, these compounds provide antimicrobial activity without damaging the dialysis membrane. At high levels, however, chlorous acid and its degradation products react with the carbon-oxygen bonds of many membranes, particularly cellulosic membranes, resulting in weakening of the membrane and ultimately in perforations thereof.

Chlorous acid ($HClO_2$) is generated in the sterilants of this invention by reacting a protic acid (HA) with a chlorite ion ($ClO_2^-$), as shown below:

$$HA + ClO_2^- \rightarrow HClO_2 + A^-$$

The chlorous acid thus generated is believed to degrade to a series of oxidizing species. In the absence of significant levels of chloride ion, this degradation is believed to proceed primarily according to the following reactions:

$$HClO_2 + ClO_2^- \rightarrow HOCl + ClO_3^-$$

$$HOCl + HClO_2 \rightarrow Cl_2O_2 + H_2O$$

$$Cl_2O_2 + HClO_2 \rightarrow Cl^- + 2ClO_2 + H^+$$

$$ClO_2 + ClO_2^- \rightleftharpoons Cl_2O_4^-$$

The transient species (e.g., HOCl and $Cl_2O_2$) and more stable oxidizing species (e.g., $ClO_2$ and $Cl_2O_4^-$) are believed to be responsible for the cidal activity of the sterilants of this invention. Lower levels of chlorous acid and chlorite ion correspond to exponentially decreased cidal activity, paralleling the lower rates of formation of the cidal oxidants.

The rate of chlorous acid degradation in the absence of significant levels of chloride ion is defined by the following equation (I):

$$\frac{-d[HClO_2]}{dt} = K_1[HClO_2]^2 + K_2[HClO_2][ClO_2^-] \quad (I)$$

Thus, the rate of chlorous acid degradation is more than second order with respect to the concentration of chlorous acid. For this reason, maintaining low levels of chlorous acid in the sterilant dramatically slows the production of antimicrobial oxidants.

In the presence of chloride ion ($Cl^-$), additional degradation reactions take place, resulting in chlorine ($Cl_2$) as an additional active oxidant as shown below:

$$Cl^- + HClO_2 + H^+ \rightarrow 2HOCl$$

$$Cl^- + HOCl + H^+ \rightarrow Cl_2 + H_2O$$

$$Cl_2 + HClO_2 \rightarrow Cl^- + Cl_2O_2 + H^+$$

$$Cl_2O_2 + HClO_2 \rightarrow Cl^- + 2ClO_2 + H^+$$

$$ClO_2 + ClO_2^- \rightleftharpoons Cl_2O_4^-$$

The empirical rate equation for the degradation of chlorous acid is significantly more complex in the presence of chloride ion, as defined below by equation (II):

$$\frac{-d[HClO_2]}{dt} = K_1[HClO_2]^2 + \frac{K_2[HClO_2][Cl^-]^2}{K_3 + [Cl^-]} \quad (II)$$

As shown in equation (II), chloride ion concentration is a squared term which has an exponential effect upon chlorous acid degradation.

As discussed above in the background section, previous chlorous acid generating sterilants, such as RenNew-D, may damage dialysis membranes. This is now believed to be due to the low pH of such sterilants (about 2.9 for RenNew-D), in combination with chloride ion, and which resulted in the rapid degradation of chlorous acid. While normally chloride ion was not a significant component of the sterilant itself, a solution of physiological saline (0.9% sodium chloride) was routinely introduced into the sterilized dialyzer immediately prior to patient hookup to displace the sterilizing solution and adjust the osmotic pressure of the liquid in the dialyzer to match that of blood. The chloride ion in the saline solution triggered the rapid formation of high levels of oxidants at the interface between the displacing saline and the displaced chlorous acid sterilant. Ordinarily such oxidants, at the lower levels associated with slower chlorous acid degradation in the sterilant, will react with nearby dissolved oxychlorine species and proceed inexorably to chlorine dioxide ($ClO_2$) formation. At the higher levels associated with chloride ion-triggered degradation at the interface between the displacing saline and displaced sterilant, however, the oxidants also reacted with labile carbon-oxygen bonds of cellulosic and other membranes. This led to the formation of holes in the dialysis membranes after repeated disinfection and displacement of the sterilant with saline.

Accordingly, the present invention discloses chlorous acid generating compositions, as well as methods relating to the use thereof, which are effective in sterilizing a dialyzer for reuse by a dialysis patient, but which do not compromise membrane integrity. These compositions and methods are particularly suited for use as dialyzer sterilants.

In one embodiment of this invention, the chlorous acid generating composition is an aqueous sterilant solution containing a protic acid and a metal chlorite, and wherein the sterilant has a pH above about 2.3 and no greater than 4.2. Such compositions may be generated by mixing appropriate amounts of a protic acid and a metal chlorite in water. Preferably, the protic acid and the metal chlorite are individually dissolved in water and packaged as a two-part system. Each part is then mixed, preferably in equal volumes, prior to use. Alternatively, one or both components may be in a solid form and dissolved in water to generate the sterilant immediately prior to use.

In this embodiment, the protic acid and metal chlorite components are present in the sterilant at concentrations such that the pH of the sterilant does not exceed 4.2. In general, the amount of metal chlorite present in the sterilant ranges from 0.01% to 1.0% by weight, preferably from 0.01% to 0.5% by weight, and more preferably from 0.02% to 0.3% by weight. Similarly, the amount of protic acid in the sterilant ranges from 0.01% to 6.0% by weight, such that the pH of the sterilant does not exceed pH 4.2 (or fall below about pH 2.3). It will be appreciated that the amount of protic acid necessary to satisfy the pH requirement will vary depending upon the strength of the acid used. For example, a smaller amount of a stronger acid (such as phosphoric acid) is needed compared to a larger amount of a weaker acid (such as lactic acid) to impart the same pH to the sterilant.

In order to fully understand the use of the above sterilant in the methods of this invention, an understanding of the various components of a dialyzing apparatus is helpful. One such apparatus commonly used in hemodialysis centers is illustrated in FIG. 1. Blood from a patient (represented by arrow 2) travels, with the aid of pump 6, into dialyzer 1 via blood inlet 7 where it is cleansed. The cleansed blood then exits dialyzer 1 via blood outlet 8, and then travels back to the patient (represented by arrow 3).

Within the dialyzer are thousands of hollow cellulosic fibers (not shown) through which the blood flows, and which are specially designed to remove excess fluid and impurities from the blood. Fresh dialysate solution (represented by arrow 4) enters dialyzer 1 via dialysate inlet 9, travels counter-current to the direction of blood flow within the hollow fibers, and spent dialysate solution (represented by arrow 5) exits the dialyzer via dialysate outlet 10. The various pumps which control the flow of dialysate through the dialysate conduits (not shown) are known to those skilled in this field.

The dialyzer itself may generally be characterized as a dual-chamber dialyzer having a dialysis membrane which separates the blood side from the dialysate side of the dialyzer, and wherein the dialysis membrane has a blood contact surface and a dialysate contact surface. While a single dialyzer typically has many thousands of hollow-fiber membranes (thus many thousands of blood contact surfaces and dialysate contact surfaces), they are typically composed of a single membrane material, and are collectively referred to herein as the dialysis membrane.

In a method of this invention, the blood contact surface and the dialysate contact surface of a dialysis membrane (i.e., the blood and dialysate sides of the dialyzer) are contacted with a sterilant of this invention having a pH between about 2.3 and 4.2. Both surfaces of the membrane are contacted with an effective amount of the sterilant, and for a sufficient period of time, to sterilize the membrane surfaces. With existing dialyzers, the quantity of sterilant to fill both the blood and dialysate sides of the dialyzer typically ranges from 60 to 150 ml, and the time of contact generally ranges in excess of 24 hours, and typically ranges from 48 to 96 hours. Contacting both surfaces of the dialysis membrane with sterilant is preferably accomplished by connecting dialysate outlet 10 of dialyzer 1 (see FIG. 1) to blood inlet 7, and filling the dialyzer via dialysate inlet 9 until sterilant exits blood outlet 8. Blood outlet 8 and dialysate inlet 9 may then be sealed and the dialyzer stored until needed for reuse by the same patient.

After contacting both surfaces of the dialysis membrane with sterilant, the sterilant on the dialysate side of the dialyzer may be replaced with an aqueous solution having a pH greater than about 6.0, such that the pH of the sterilant on the blood side of the dialyzer increases to at least about 5.0. In this embodiment, replacement of the dialysate may be achieved by displacement. Alternatively, the dialysate may be drained prior to contacting the dialysate side of the dialysis membrane with the aqueous solution.

Replacement is most readily accomplished by connecting dialysate inlet 9 to a source of the aqueous solution, and displacing the sterilant on the dialysate side with the aqueous solution until it exits dialysate outlet 10. The aqueous solution is then maintained within the dialysate side of the dialyzer for a period of time sufficient to cause the pH of the sterilant on the blood side of the dialyzer to increase to at least about 5.0. Such a pH increase of the sterilant on the blood side is the result of diffusion of the hydrogen ions from the blood side to the dialysate side of the dialyzer. This results in the conversion of chlorous acid on the blood side to chlorite species e.g., sodium chlorite ions) in a near-neutral environment. The sterilant on the blood side having the increased pH ms referred to herein as the "pH-adjusted sterilant."

Preferably, the aqueous solution contains alkali ions. Any alkali ion-containing solution may be used to replace the dialysate, provided that the pH of the sterilant on the blood side of the dialyzer increases to at least about 5.0. The pH of the aqueous alkali ion-containing solution preferably ranges from 6.0 to 8.0, and more preferably from 6.5 to 7.5, and most preferably is 7.0. The time period generally sufficient to increase the pH of the sterilant on the blood side ranges from 1 to 10 minutes, and typically from 2 to 5 minutes.

Those of ordinary skill in the art will appreciate that the pH and the buffering capacity of the alkali ion-containing solution that is necessary to adequately raise the pH of the sterilant on the blood side will vary, depending on the pH and total acid content of the sterilant used. Preferably, the aqueous alkali ion-containing solution is an alkali ion-containing buffer solution (such as the powdered or liquid concentrate forms sold under the trade names NaturaLyte 4000 Dry Pack, NaturaLyte 6000 Dry Pack, the NaturaLyte 4000 & 6000 Rx series, and NaturaLyte Liquid Bicarbonate by National Medical Care, Rockleigh, N.J.).

In a preferred embodiment, the pH of the sterilant is between about 3.3 and 4.2, more preferably from 3.5 to 4.2, and most preferably from 3.6 to 4.0. In this embodiment, the sterilant on the dialysate side of the dialyzer may be replaced with a weakly buffered solution, such as dialysate. At a pH of 3.3, the percentage of chlorite ion present in the sterilant as chlorous acid is approximately 4.4%. This percentage decreases as the pH increases, and drops to approximately 0.6% at a pH of 4.2. Accordingly, control of the pH so that it remains between 3.3 and 4.2 maintains a level of chlorous acid that ranges between approximately 0.5% and 5.0% by weight. Within this range, displacement of the sterilant with a dialysate solution (having a pH in excess of about 6.0) is sufficient to raise the pH on the blood side to at least 5.0.

The dialysate solution is more preferably an isotonic dialysate solution having a combined acetate/bicarbonate buffer, and a pH of about 7.2 to 7.6. The preferred approximate ionic content of the dialysate solution is as follows: 0.0–3.0 meq/L potassium; 137–140 meq/L sodium; 0.0–3.5 meq/L calcium; 0.7–1.5 meq/L magnesium; 3.0–4.0 meq/L acetate; 101–111 meq/L chloride; 32–35 meq/L bicarbonate; and 0.0–2.5 gm/L dextrose. By employing such a sterilant, a practitioner at a hemodialysis center need only reverse the set-up procedures presently employed for reprocessing dialyzers using existing, commercially available sterilants (i.e., in this case, the saline displacement of sterilant on the blood side follows the dialysate solution displacement on the dialysate side of the dialyzer).

Alternatively, when the pH of the sterilant ranges from about 3.3 to 4.2, the sterilant on the dialysate side of the dialyzer may be replaced with water, such as reverse osmosis (RO) water. The RO water is maintained on the dialysate side of the dialyzer for a period of time sufficient to raise the pH of the sterilant on the blood side of the dialyzer to at least 5.0.

After replacing the sterilant on the dialysate side with the aqueous solution, the pH-adjusted sterilant on the blood side is then replaced with an isotonic saline solution. Preferably, the pH-adjusted sterilant is displaced with the isotonic saline solution in a manner such that air bubbles are not introduced into the blood side of the dialyzer. This may be accomplished by connecting blood inlet 7 to a source of the isotonic saline solution, and displacing the sterilant on the blood side with the isotonic saline until it exits blood outlet 8. By converting the chlorous acid on the blood side to alkali-chlorite species prior to saline displacement of the same, membrane damage caused by the degradation of chlorous acid to membrane-corroding oxidants is avoided. It should be noted that the dialysate side is not flushed with saline alone, and that flushing of the dialysate side first, followed by saline flushing of the blood side, represents a critical reversal of the techniques practiced in hemodialysis clinics (i.e., where the saline displacement of sterilant occurs first on the blood side, followed by dialysate solution displacement on the dialysate side of the dialyzer).

In an alternative embodiment, after contacting both surfaces of the dialysis membrane with sterilant, the sterilant on the dialysate side of the dialyzer is drained. This may be accomplished by opening the dialysate outlet 10 of the vertically-positioned dialyzer, and then opening the dialysate inlet 9 through which the sterilant exits by gravity. After draining of the sterilant from the dialysate side, an isotonic dialysate solution, such as the solution described above, may be introduced via dialysate inlet 9 and allowed to flow through the vertically-positioned dialyzer to exit through dialysate outlet 10. Thereafter, isotonic saline is introduced through the blood inlet 7 as described above.

The compositions and methods of this invention provide numerous advantages over existing, commercially available sterilants used to reprocess dialyzers. For example, the compositions of this invention provide very high antimicrobial activity against microorganisms which can contaminate dialyzers (and infect patients connected to the same), while not significantly degrading dialysis membranes. In addition, the sterilants of the present invention have no known adverse effects on the patients or technicians who might be exposed to them. The methods disclosed herein avoid the formation of membrane perforations which have heretofore caused the chlorous acid generating compositions to be discontinued from commercial use as sterilants in hemodialysis clinics.

Moreover, as discussed in greater detail in the examples below, it has been surprisingly found that use of a chlorous acid generating composition which contains higher total chlorite levels, but a lower amount of chlorite ion in the form of chlorous acid (i.e., 0.5% to 5.0%) compared to prior commercially available products (such as RenNew-D, wherein 10% of the chlorite was in the form of chlorous acid), results in superior sterilizing properties. Heretofore, the disinfecting action of acidified chlorite systems has been ascribed directly to the action of the chlorous acid formed upon such acidification. In addition, such sterilants have been found to not significantly degrade dialysis membranes. Thus, the combination of superior disinfecting properties with membrane integrity makes the sterilants of this invention ideally suited for use as reprocessing sterilants for dialyzers.

The present invention is illustrated by reference to the following examples, which are to be regarded as illustrative rather than restrictive. All parts and percentages in the examples, as well as in the claims and specification, are by weight unless otherwise indicated.

EXAMPLES

Example 1

Comparison of Membrane Integrity after Exposure of a Dialysis Membrane to Chlorous Acid Sterilants at Low and High pH This Example compares dialysis membrane integrity after sterilization with a chlorous acid generating composition having a pH lower than 3.3 with the integrity after sterilization with a composition at higher pH. In this Example, the pH of the sterilant on the blood side of the dialyzer was not raised prior to displacement of the same with saline (i.e., the saline displacement of sterilant on the blood side occurred first, followed by dialysate solution displacement on the dialysate side of the dialyzer).

In a first experiment, sterilization was performed using the sterilant RenNew-D, which had a pH of about 2.9, and wherein the chlorite ion concentration in the form of chlorous acid was about 10% by weight of the total amount of the chlorite ion in the sterilant. The RenNew-D solution was capable of being stored for many weeks in cellulose and cellulose acetate hollow-fiber membrane dialyzers, with no discernible hole formation. The determination of whether hole formation occurred was made by filling the dialysate side of a used and reprocessed dialyzer with a bacterial inoculum (e.g., *Pseudomonas aeruginosa*), and determining whether any of these organisms could be found in a culture medium of the aqueous liquid taken from the blood side of the dialyzer after standing overnight.

Despite the lack of discrete hole formation, the RenNew-D solution had a general weakening effect on cellulose-based dialyzers repeatedly exposed to the sterilant. This weakening effect became evident as a result of pressure-decay testing of dialyzers following exposure to the sterilant. Such testing measures the reduction in integrity of a dialyzer membrane as evidenced by loss of pressure of a pressurized dialyzer's blood tubing 30 seconds after pressurization with air to 300 mm Hg. The average of replicate runs, after a series of multiple exposures to the sterilant, is compared with the original pressure decay after exposure to water. When a pressure decay of 30 mm Hg or more is observed, it is believed that perforations in the membrane account for that magnitude of pressure loss.

Eight Clirans Model TAF15M cuprammonium rayon dialyzers were exposed to the pH 2.9 chlorous acid system (i.e., RenNew-D) for periods up to 67 days. After this exposure, pressure decays increased from an average 8 mm Hg (measured prior to exposure to RenNew-D) up to a 28 mm Hg maximum for seven of the eight dialyzers, and a 34 mm Hg maximum for the eighth. The eighth dialyzer exceeded the threshold of possible hole formation (30 mm Hg), but no holes were found following exposure of the blood tubing to a bacterial inoculum. The pressure decay is believed to derive from the low level creation of oxidants during the slow degradation of the chlorous acid in the solution, and their erosive action on the membranes.

In a second experiment, twenty similar dialyzers were exposed to a 5.1-fold higher-concentrated chlorite solution (i.e., 2,525 ppm vs. 496 ppm for RenNew-D), but at a higher pH of 4.0. The pressure-decay for the twenty dialyzers exposed to the pH 4.0 solution, at an initial average of 6 mm Hg, never exceeded 16 mm Hg after 50 days exposure, and none crossed the threshold of possible hole formation (30 mm Hg). Accordingly, by raising the pH of the sterilant from 2.9 to 4.0, the integrity of the dialyzer membrane is significantly improved.

Figure 2:
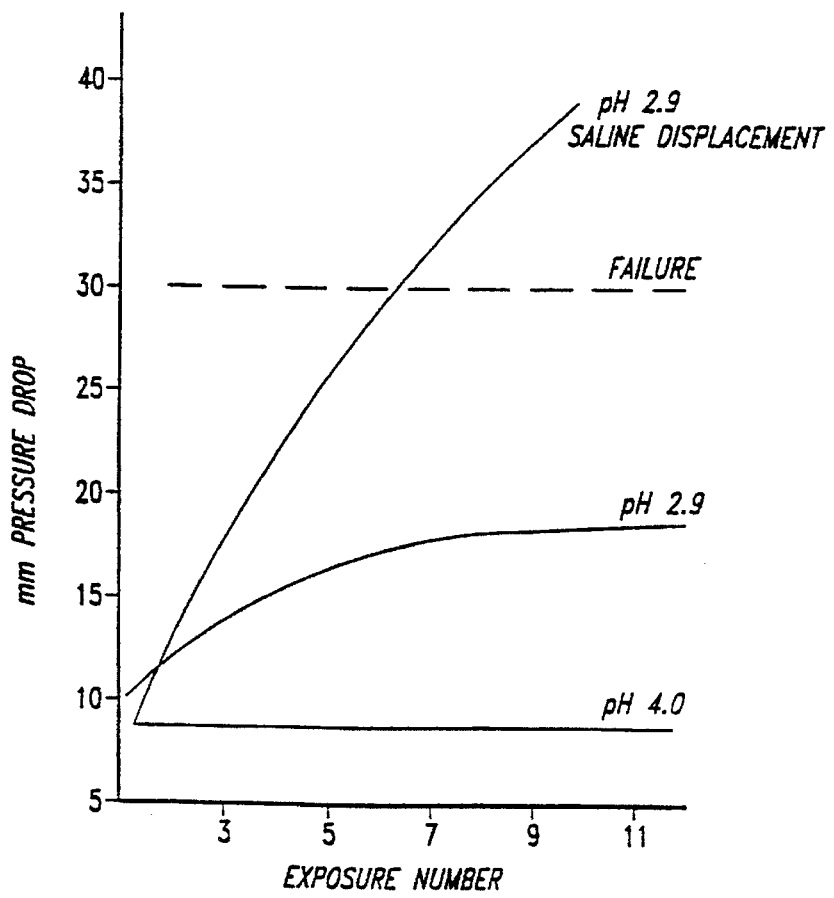
FIG. 2 is a plot of pressure drop across a dialysis membrane as a function of the number of exposures to different sterilant compositions.

The pressure decay for dialyzers repeatedly exposed to the pH 2.9 and pH 4.0 sterilants was also evaluated. The dialyzers exposed to the higher pH sterilant had a vastly improved pressure decay rate, as illustrated in FIG. 2. Specifically, FIG. 2 is a plot of the average pressure decay observed for both the pH 2.9 sterilant and the pH 4.0 sterilant over the course of 11 exposures, where each exposure was followed by draining, washing and replacing of the sterilant. At pH 4.0, the percentage of total chlorite as chlorous acid was 0.8%, so in comparison with the pH 2.9, less-concentrated RenNew-D formula, the pH 4.0 solution had a $(5.1/1) \times (0.8\%/10\%) = 0.41$ times lower chlorous acid concentration. After 11 exposures, the dialyzer exposed to the pH 4.0 sterilant showed almost no change in pressure-decay, whereas the pH 2.9 sterilant resulted in a change in pressure-decay from an average of 9 mm Hg to about 18 mm Hg. None of the individual dialyzers in each group showed a probable failure, by exceeding a 30 mm pressure drop.

Also shown in FIG. 2 is the average pressure decay observed for the pH 2.9 sterilant over the course of 10 exposures, where each exposure was followed by saline displacement of the sterilant. Average membrane failure occurred after only 7 exposures, with individual dialyzers failing before that time. This demonstrates that saline displacement of the sterilant results in rapid weakening and perforation of the dialyzer membrane.

The major improvement in membrane integrity that results from increasing the pH of the sterilant from 2.9 to 4.0 can be directly correlated with the exponential increase in chlorous acid stability in the higher chlorite/lower chlorous acid solution of pH 4.0. The relative decay rate of the pH 4.0 solution, as compared to the pH 2.9 solution, assuming merely second-order kinetics according to equation (I) (i.e., ignoring the contribution of the second term), is at least the square of the relative chlorous acid levels. That is $(1)^2 + (0.41)^2$ or 5.9 times less, even with a more than five-fold greater amount of total chlorite.

Surprisingly, the pH 4.0 solution also displayed a greater antimicrobial activity than the pH 2.9 solution, even though it had only 41% of the chlorous acid content. This greater activity was manifest in the so-called "D-values" of the two solutions—that is, the time required to reduce a challenge bacterial inoculum by 90% (one logarithm). Using a *Bacillus subtilis* spore inoculum, the D-value of the pH 4.0 solution was a more-efficient 1.4 minutes, vs. the 4.8 minutes for the pH 2.9 solution that had a 12.5-fold higher relative chlorous acid. Thus, reprocessing using the compositions of this invention resulted in improved membrane integrity and superior disinfection.

Example 2

Disinfection of a Hemodialyzer with a Chlorous Acid Generating Sterilant

This Example illustrates the preparation of a chlorous acid composition and the use of that composition to sterilize used hemodialyzers without causing any long-term adverse effects on the integrity of the dialysis membrane, as measured by excessive increases in pressure decay of the treated pressurized dialyzers.

An aqueous solution was prepared containing 3.03% sodium chlorite and 1.37% tetrasodium EDTA. One part of this solution was combined with eleven parts of an aqueous solution containing 0.38% lactic acid, 1.68% sodium hydroxide, and 0.04% sodium benzoate. The resulting mixed solution had a pH of 4.0, and was introduced into the blood-tubing side (7) of a previously-used dialyzer, from which it passed directly to the dialysate side (9), as part of a reprocessing operation, after the dialyzer tubing had been flushed with water to eliminate soluble and suspended blood products.

This solution had a chlorite ion content in the form of chlorous acid of 0.8% with respect to total chlorite ion content in solution, and had a D-value of 1.4 minutes against *B. subtilis* spores. When used to sterilize a cuprammonium-cellulose hemodialyzer in a series of ten sequential reprocessing operations, this sterilant solution caused an increased pressure decay of no greater than 5 mm Hg, as compared with the initial value, when measured 30-seconds after pressurization of the hemodialyzer to 300 mm Hg.

Example 3

Disinfection of a Hemodialyzer with a Chlorous Acid Generating Sterilant

In this Example, Example 2 is repeated using a composition prepared by combining one part of an aqueous solution of 1.52% sodium chlorite, 0.10% sodium dodecylbenzenesulfonate and 0.57% tetrasodium EDTA with fourteen parts of an aqueous solution of 0.10% mandelic acid and 0.04% sodium benzoate to form a hemodialyzer sterilant of pH 3.56, and wherein about 2.5% of the total chlorite ion is in the form of chlorous acid.

Example 4

Disinfection of a Hemodialyzer with a Chlorous Acid Generating Sterilant

Example 3 is repeated except that 1.00% sodium chlorite is used in place of the 1.52% sodium chlorite. When one part of this solution is combined with fourteen parts of the mandelic acid solution of Example 3, a hemodialyzer sterilant solution is formed with a pH of 3.3, where about 5.0% of the total chlorite ion is in the form of chlorous acid.

Example 5

Disinfection of a Hemodialyzer with a Chlorous Acid Generating Sterilant

Example 3 is again repeated, except that the mandelic acid is replaced with 0.1% malic acid to form a sterilizing composition for hemodialyzers which has an equivalent sterilizing effectiveness and a pH of 3.4.

Example 6

Disinfection of a Hemodialyzer using a pH 4.0 Sterilant and Preserving Membrane Integrity After disinfecting a hemodialyzer as in Example 2, the sterilant is removed from a reprocessed hemodialyzer. This is accomplished by connecting a stream of RO (reverse-osmosis) water to the dialysate inlet and allowing 1 liter of water to flow through the dialysate side of the hemodialyzer. Pyrogen-free sterile saline is then allowed to flow through the blood tubing of the dialyzer, and the RO water on the dialysate side is replaced with dialysate solution. Both flows continue until replacement of both sterilant and water is complete, using about 1 liter each of saline and dialysate. Thereafter, in order to initiate the dialysis process, the patient's blood supply is connected to the blood tubing side of the dialyzer, while the dialysate fluid is flowing through the dialysate side of the membrane dialyzer.

Example 7

Disinfection of a Hemodialyzer using a pH 4.0 Sterilant and Preserving Membrane Integrity After disinfecting a hemodialyzer as in Example 2, the sterilant is removed by first draining the dialysate side of the hemodialyzer free of sterilant and then flushing a buffered dialysate through the dialysate side of the dialyzer in a sufficient quantity so as to osmotically neutralize the acidity of the sterilant in the blood side of the tubing. Thereafter a pyrogen-free physiological saline solution is flushed through the blood tubing to completely displace the residual components of the neutralized sterilant. While continuing the flow of buffered dialysate, the patient's blood supply is connected to the saline-flushed blood tubing to initiate the dialysis process.

From the foregoing, it will be evident that although specific embodiments of the invention have been described herein for the purpose of illustrating the invention, various modifications may be made without deviating from the spirit and scope of the invention.

I claim:

1. A method for disinfecting a dual-chamber hemodialyzer having a blood side and a dialysate side separated by a dialysis membrane, wherein the membrane has a blood contact surface and a dialysate contact surface, comprising:

(a) contacting a blood contact surface and a dialysate contact surface of a dialysis membrane with an effective amount of an aqueous sterilant comprising a protic acid and a metal chlorite, and wherein the sterilant has a pH ranging from about 2.3 to 4.2;

(b) replacing the sterilant in contact with the dialysate contact surface of the dialysis membrane with an aqueous solution such that the pH of the sterilant in contact with the blood contact surface of the dialysis membrane increases to at least about 5.0 to yield a pH-adjusted sterilant; and (c) subsequently replacing the pH-adjusted sterilant in contact with the blood contact surface of the dialysis membrane with an isotonic saline solution.

2. The method of claim 1 wherein the aqueous solution contains an alkali ion.

3. The method of claim 1 wherein the sterilant in contact with the dialysate contact surface is displaced with the aqueous solution.

4. The method of claim 1 wherein the aqueous solution is a buffer solution having a pH ranging from 6.0 to 8.0.

5. The method of claim 1 wherein the metal chlorite concentration ranges from 0.01% to 1.0% by weight of the sterilant.

6. The method of claim 1 herein the metal chlorite concentration ranges from 0.01% to 0.5% by weight of the sterilant.

7. The method of claim 1 herein the metal chlorite concentration ranges from 0.02% to 0.3% by weight of the sterilant.

8. The method of claim 1 wherein the metal chlorite is sodium chlorite.

9. The method of claim 1 wherein the protic acid concentration ranges from 0.01% to 6% by weight of the sterilant.

10. The method of claim 1 where the protic acid is an organic acid.

11. The method of claim 10 wherein the organic acid has a pK ranging from 2.8 to 4.2.

12. The method of claim 10 wherein the organic acid is selected from the group consisting of citric acid, lactic acid, malic acid, tartaric acid, glycolic acid, mandelic acid, and mixtures thereof.

13. The method of claim 1 wherein the protic acid is an inorganic acid.

14. The method of claim 13 wherein the inorganic acid is selected from the group consisting of sulfuric acid, hydrochloric acid, nitric acid, phosphoric acid, and mixtures thereof.

15. The method of claim 1 wherein the protic acid is malic acid and the metal chlorite is sodium chlorite.

16. The method of claim 1 wherein the dialysis membrane is a cellulosic or cellulosic ester membrane.

17. The method of claim 1 wherein the pH of the sterilant of step (a) ranges from about 3.3 to 4.2.

18. A method for disinfecting a dual-chamber hemodialyzer having a blood side and a dialysate side separated by a dialysis membrane, wherein the membrane has a blood contact surface and a dialysate contact surface, comprising:
  (a) contacting a blood contact surface and a dialysate contact surface of a dialysis membrane with an effective amount of an aqueous sterilant comprising a protic acid and a metal chlorite, and wherein the sterilant has a pH ranging from about 2.3 to 4.2;
  (b) displacing the sterilant in contact with the dialysate contact surface of the dialysis membrane with an aqueous alkali ion-containing solution having a pH greater than about 6.0, such that the pH of the sterilant in contact with the blood contact surface of the dialysis membrane increases to at least about 5.0 to yield a pH-adjusted sterilant; and
  (c) subsequently displacing the pH-adjusted sterilant in contact with the blood contact surface of the dialysis membrane with an isotonic saline solution.

19. The method of claim 18 wherein the aqueous alkali ion-containing solution is a buffer solution having a pH ranging from 6.0 to 8.0.

20. The method of claim 18 wherein the pH of the sterilant ranges from about 3.3 to 4.2.

21. A method for disinfecting a dual-chamber hemodialyzer having a blood side and a dialysate side separated by a dialysis membrane, wherein the membrane has a blood contact surface and a dialysate contact surface, comprising:
  (a) contacting a blood contact surface and a dialysate contact surface of a dialysis membrane with an effective amount of an aqueous sterilant comprising a protic acid and a metal chlorite, wherein the sterilant has a pH ranging from about 3.3 to 4.2, and wherein the amount of chlorite ion present in the form of chlorous acid ranges from 0.5% to 5.0% by weight of the total amount of chlorite ion in the sterilant;
  (b) displacing the sterilant in contact with the dialysate contact surface of the dialysis membrane with an aqueous solution, such that the pH of the sterilant in contact with the blood contact surface of the dialysis membrane increases to at least about 5.0 to yield a pH-adjusted sterilant; and
  (c) subsequently displacing the pH-adjusted sterilant in contact with the blood contact surface of the dialysis membrane with an isotonic saline solution.

22. The method of claim 21 wherein the aqueous solution is unbuffered water.

23. The method of claim 21 wherein the aqueous solution is buffered isotonic dialysate.

24. The method of claim 23 wherein the buffered isotonic dialysate solution has a pH ranging from 7.2 to 7.6.

25. The method of claim 21 wherein the pH of the sterilant ranges from 3.5 to 4.2.

26. The method of claim 21 wherein the pH of the sterilant ranges from 3.6 to 4.0.

* * * * *